United States Patent [19]

Baeker

[11] 4,357,708
[45] Nov. 2, 1982

[54] X-RAY DIAGNOSTIC SYSTEM COMPRISING TOMOGRAPHIC APPARATUS

[75] Inventor: Klaus Baeker, Uttenreuth, Fed. Rep. of Germany

[73] Assignee: Siemens Aktiengesellschaft, Berlin and Munich, Fed. Rep. of Germany

[21] Appl. No.: 197,075

[22] Filed: Oct. 15, 1980

[30] Foreign Application Priority Data

Nov. 23, 1979 [DE] Fed. Rep. of Germany ....... 2947354

[51] Int. Cl.³ .......................................... G03B 41/16
[52] U.S. Cl. ...................................... 378/25; 378/27; 378/91
[58] Field of Search ..................... 250/44 ST, 402, 413

[56] References Cited

U.S. PATENT DOCUMENTS 4,039,836  8/1977  Shaw ................................. 250/402

FOREIGN PATENT DOCUMENTS 2116705  5/1977  Fed. Rep. of Germany .

Primary Examiner—Craig E. Church
Attorney, Agent, or Firm—Hill, Van Santen, Steadman, Chiara & Simpson

[57] ABSTRACT

In the exemplary embodiments the path of movement of the photographic exposure unit comprised of an x-ray tube and image layer (or film) carrier can be selected. For determination of the photographic exposure time, either an mAs-relay or an automatic exposure timer with a radiation detector may be placed in control of the energization of the x-ray tube. The x-ray tube current or the current of the radiation detector are integrated and the integrator contents are sampled at a predetermined time following commencement of the photographic exposure. The sampled value is compared with a reference value and the running speed of the photographic exposure unit is influenced in such a fashion that the photographic exposure time determined by the switching of the mAs-relay or by the automatic exposure timer approximately corresponds to the running time of the photographic exposure unit.

4 Claims, 1 Drawing Figure

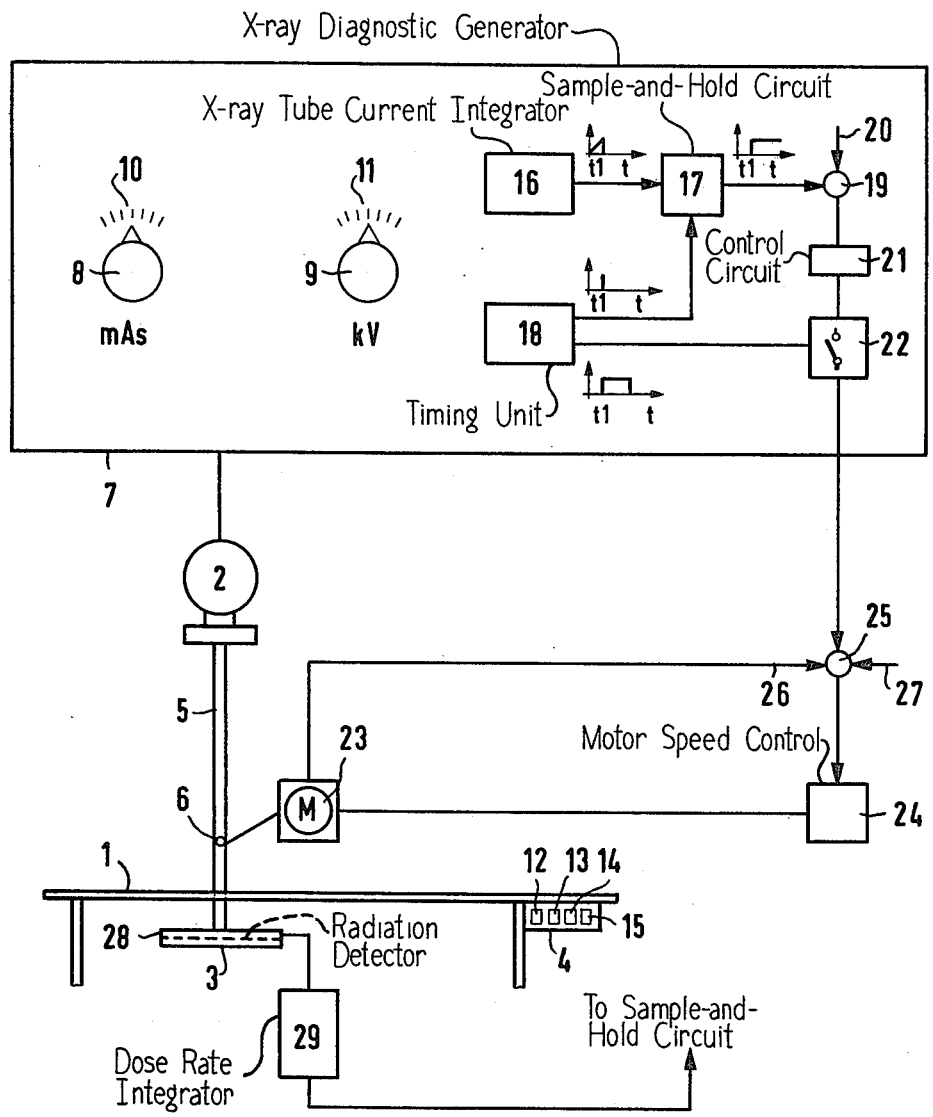

X-RAY DIAGNOSTIC SYSTEM COMPRISING TOMOGRAPHIC APPARATUS

BACKGROUND OF THE INVENTION

The invention relates to an x-ray diagnostic system comprising a tomograph with which means are associated for the selection of the path of movement of the photographic exposure unit (through which selection the running time of photographic exposure unit is also determined), the photographic exposure unit including an x-ray tube and image layer (or film) carrier, and the system further comprising an x-ray diagnostic generator for supplying the x-ray tube and which contains input means for setting the photographic exposure data.

An x-ray diagnostic system of this type is described in the German OS No. 21 16 705. In the case of this x-ray diagnostic system, four different paths of movement, and, accordingly, four different running times of the photographic exposure unit are selectable. The x-ray diagnostic generator permits the adjustment of the mAs-product and the x-ray tube voltage for a photographic exposure.

Optimum photographic exposures are obtained only if the photographic exposure time during which high voltage is supplied to the x-ray tube is approximately equal to the running time which elapses during movement of the photographic exposure unit over the selected path. However, in practice, in the known x-ray diagnostic system the photographic exposure time will always be somewhat shorter than the running time of the photographic exposure unit, since the x-ray tube must be reliably switched off before the movement of the photographic exposure unit is terminated.

SUMMARY OF THE INVENTION

The object underlying the invention resides in designing an x-ray diagnostic system of the type initially cited such that the photographic exposure time is always approximately equal to the running time for completing the path of movement of the photographic exposure unit.

In accordance with the invention, this object is achieved in that means are present for the formation of a signal which corresponds to a photographic exposure value determining the photographic exposure time, and that a control circuit is present for controlling the speed of movement of the photographic exposure unit and which control circuit influences such speed of movement in dependence upon this signal, in such a fashion that the running time approximately corresponds to the actual photographic exposure time. In the inventive x-ray diagnostic system, immediately following commencement of a photographic exposure, inference is made as to the necessary photographic exposure time from the measured photographic exposure value, and the running time is so influenced that the running for the complete movement cycle will be approximately equal to the total photographic exposure time.

An expedient embodiment of the invention provides an mAs-relay with an integrator for the x-ray tube current for the determination of the photographic exposure time, and a comparator circuit for comparing the contents of the integrator, which have been attained after a specific time following the commencement of the photographic exposure, with a reference signal; the comparator influences the running speed of the photographic exposure unit via the control circuit, in dependence upon the difference of its input signals. In this embodiment of the invention, after expiration of a specific time following commencement of the photographic exposure, an mAs-product value which has been attained during the interval is obtained and this measured mAs-product value is compared with the appropriate reference value. If the measured and reference magnitude correspond, then no change in the running speed of the photographic exposure unit takes place. Otherwise the running speed is influenced with the object of achieving an approximate matching of the running time to the photographic exposure time. Instead of an mAs-relay, an automatic exposure timer for determination of the photographic exposure time can also be present which exhibits a radiation detector for supplying a current which is dependent upon the dose rate beyond the radiography subject, and an integrataor for integrating this current as a function of time. In this case, also, after a speific time following commencement of the photographic exposure, the contents of the intergrator can be compared with a reference signal and the running speed can be influenced in dependence upon the comparison result.

The invention shall be explained in greater detail in the following on the basis of an exemplary embodiment illustrated in the FIGURE on the accompanying drawing sheet; and other objects, features and advantages will be apparent from this detailed disclosure and from the appended claims.

BRIEF DESCRIPTION OF THE DRAWING

The single FIGURE is a diagrammatic view showing an x-ray diagnostic system in accordance with the present invention.

DETAILED DESCRIPTION

In the drawing an x-ray tomograph is illustrated which exhibits a patient support 1, an x-ray tube 2, an image layer (or film) carrier 3, and a selector panel 4. The x-ray tube 2 and the image layer carrier 3 are interconnected through a rod 5 which is pivotal about a pivot axis at 6. Through reciprocal movement of the x-ray tube 2 and the image layer carrier 3, photographic exposures of a specific longitudinal body layer of a patient, supported on the patient support plate 1, can be prepared.

The supply and control of the tomograph proceeds by means of an x-ray diagnostic generator 7 which includes a selector knob 8 for setting the mAs-product and a selector knob 9 for selecting the x-ray tube voltage. The respectively adjusted mAs-product is displayed on a scale 10 (in milliampere-seconds), and the respectively adjusted x-ray tube voltage is displayed on a scale 11 (in kilovolts).

The selector panel 4 exhibits four keys 12 through 15 for selection of the path of movement of the x-ray tube 2 and of the image layer carrier 3. Through the key 12, for example, an elliptical path of movement is selected in which the running time of the photographic exposure unit 2, 3 amounts to five seconds (5 sec); through the key 13, for example, a linear path of movement for image-formation of a thin body layer with a running time of one and two-tenths seconds (1.2 sec) is selected; through the key 14, for example, a linear path of movement for the image-formation of a thick body layer with a running time of six-tenths of a second (0.6 sec) is selected; and, through the key 15, for example, a circular path of movement with a running time of two and one-half seconds (2.5 sec) is selected.

The photographic exposure values are so adjusted by the user that, within the respective running time of the photographic exposure unit 2, 3, approximately the adjusted mAs-product is obtained. The mAs-relay of the x-ray diagnostic generator 7 exhibits an mA-integrator 16 which integrates the x-ray tube current as a function of time. At every time point following commencement of a photographic exposure, the contents of the mA-integrator 16 are thus a measure of the attained mAs-product. A signal corresponding to the contents of the mA-integrator 16 is supplied to a sample-and-hold circuit 17 which is controleld by a timing unit 18. The timing unit 18 supplies an output signal to the sample-and-hold circuit 17, for example, after a time (t1) of thirty milliseconds (30 msec) following commencement of the photographic exposure, for effecting sampling of the contents of the mA-integrator; i.e., for sampling of the mAs-product attained after this time. The mAs value stored in the sample-and-hold circuit 17 is supplied to a comparator 19 which compares it with a reference value at the input 20. If the values deviate from one another, an influencing of the motor 23 which drives the photographic exposure unit 2, 3, takes place via a control circuit 21 and a switch 22.

In the instance in which the mAs-value attained in the time t1 is smaller than the reference value, the running speed of the motor 23, and hence of the photographic exposure unit 2, 3, is reduced; in the instance in which the mAs-product attained in the time t1 is greater than the reference value, the running speed is increased, so that the photographic exposure time determined by the mAs-relay (and as selected at 8) is approximately equal to the running time of the photographic exposure unit 2, 3.

Motor 23 is speed-controlled. For this purpose, a speed controlling device 24 is provided to which a signal is supplied from a comparator 25 which determines the difference between a signal connected to the input 26, corresponding to the actual value of the speed, and a signal connected to the input 27, corresponding to a nominal setpoint value of the speed. There is supplied to the comparator 25, via a switch 22, the output signal of the control circuit 21 for the purpose of influencing the input signal of the control device 24 with the object of changing the motor speed, said switch 22 being closed by the timing unit 18 from the time t1 until the end of a photographic exposure.

Instead of an mAs-relay, an automatic exposure timer for determining the photographic exposure time can be present which exhibits a radiation detector for the formation of a current which is dependent upon the dose rate beyond the radiography subject. This current can likewise be integrated and the integral as a function of time can be sampled and compared with a reference value at the time t1, whereby then, in the described manner, in dependence upon the comparison results, an influencing of the running speed of the photographic exposure unit 2, 3 takes place.

In the drawing the radiation detector 28 of such an automatic exposure timer is indicated in broken lines. This radiation detector is connected to an integrator 29 which, in place of the integrator 16, upon reaching a specific integrated (dose) value, effects the switching-off of the x-ray tube 2. The integrator 29, instead of the intergrator 16, can be connected to the sample-and-hold circuit 17, so that its signal, obtained at the time t1, can be compared in the manner described and, in dependence upon the comparison result, a control of the running speed of the photographic exposure unit 2, 3, can take place.

As will be understood by those skilled in the art, the reference value at 27 will set the speed of the exposure unit 2, 3 at a suitable speed to execute the movement selected at 12–15 within a running time corresponding to a standard time interval, i.e. five seconds, one and two-tenths seconds, six-tenths second, or two and five-tenths second.

Then, after the time t1 as determined by timing unit 18, the nominal setpoint value at 27 is modified (increased or decreased) by the signal from control circuit 21 to the extent found empirically necessary to correct for any discrepancy between the predicted shut-off time for the x-ray tube 2, and the normal running time for the exposure unit 2, 3. An empirical selection of the reference value 20 for each type of cycle of the exposure unit 2, 3 is clearly within the skill of the art. The respective reference values may be set on respective potentiometers, the outputs of the respective potentiometers being connected with input 20 of comparator 19 in response to actuation of the respective selector switches 12–15.

A manual selector switch may be provided for selectively activating the mAs timer including selector 8 and integrator 16, or for selectively activating a dose rate selector knob, and a dose responsive exposure control including integrator 29. In one position of such manual selector, the selected mAs value will control the duration of the x-ray exposure, while in the other position the selected exposure dose value will control the duration of the x-ray exposure, which is to be matched to the running time of the exposure unit 2, 3.

It will be apparent that many modifications and variations may be effected without departing from the scope of the novel concepts and teachings of the present invention.

I claim as my invention:

1. An x-ray diagnostic system comprising tomographic apparatus having path selection means for the selection of the path of movement, a photographic exposure unit comprised of an x-ray tube and an image layer carrier, an x-ray diagnostic generator for supplying a high voltage for energizing said x-ray tube and having means (8, 9) for the selection of exposure parameters for the photographic exposure unit to provide for an x-ray exposure during a photographic exposure time which is a function of said exposure parameters, characterized in speed controlling means for causing said photographic exposure unit to begin traversing the path of movement selected by said path selection means during an initial time interval at a given running speed selected to complete traverse of the path in a total running time equal to the expected exposure time, control signal forming means (16, 29) coupled with the tomographic apparatus for generating a control signal during said initial time interval as a function of the exposure parameter that determines the exposure time, and comparator means (25) having one input coupled with said control signal forming means for receiving a control signal generated during said initial time interval and a second input for receiving a motor signal indicating the actual speed of the exposure unit said comparator means (25) having an output for connection with said speed controlling means and being operable to compare the control signal with the motor signal and to control said speed controlling means in accordance with any deviation of said control signal relative to said motor signal to adjust the running speed of the photographic exposure unit along the selected path after the initial time interval such that the actual total running time of the photographic exposure unit along the selected path will substantially equal the photographic exposure time based on measurement of said photographic exposure parameter.

2. An x-ray diagnostic system according to claim 1, with said tomographic apparatus comprising a radiation detector (28) for supplying a current which is a function of the dose rate supplied to a patient, and controlling the photographic exposure time according to a product of dose rate and time, so that the photographic exposure parameter is the value of the dose rate, said control signal forming means comprising an integrator (29) coupled with the radiation detector (28) for forming a time integral of the value of current therefrom a second comparator (19) for receiving the contents of the integrator (29), after a specific time following commencement of the photographic exposure corresponding to said initial time interval so as to influence the running speed of the photographic exposure unit (2, 3) in dependence upon the difference between said control signal and said motor signal.

3. An x-ray diagnostic system according to claim 1, with said tomographic apparatus controlling the photographic exposure time according to a product (mAs) of x-ray tube current and time, so that the photographic exposure parameter is the value of x-ray tube current, said control signal forming means comprising an integrator (16) for integrating the x-ray tube current and a second comparator (19) for receiving the contents of the intergrator (16) at a specific time following commencement of the photographic exposure corresponding to said initial time interval so as to influence the running speed of the photographic exposure unit (2,3) in dependence upon the difference between said control signal and said motor sigal.

4. An x-ray diagnostic system according to claim 3, characterized in that a timing unit (18) is operative to provide an output at a specific time (t1) following the commencement of a photographic exposure, and a sample-and-hold circuit (17) is connected between an input of the second comparator (19) and an output of the integrator (16), said sample-and-hold circuit being controlled in response to said output from said timing unit (18) for the purpose of storage of the integrator contents.

* * * * *